United States Patent [19]
Weijand et al.

[11] Patent Number: 5,989,192
[45] Date of Patent: Nov. 23, 1999

[54] CARDIAC FLOW SENSOR

[75] Inventors: Koen J. Weijand, Hoensbroek; Vincent J. A. Schouten, Cadier en Keer, both of Netherlands

[73] Assignee: Medtronic, Inc., Minneapolis, Minn.

[21] Appl. No.: 08/937,442

[22] Filed: Sep. 25, 1997

[51] Int. Cl.$^6$ .................................................. A61B 5/00
[52] U.S. Cl. ..................... 600/504; 600/505; 600/526
[58] Field of Search .................................. 600/504, 505, 600/526, 549

[56] References Cited

U.S. PATENT DOCUMENTS

| | | | |
|---|---|---|---|
| 4,384,578 | 5/1983 | Winkler | 604/114 |
| 4,796,640 | 1/1989 | Webler | 600/526 |
| 5,174,299 | 12/1992 | Nelson | 128/692 |
| 5,336,244 | 8/1994 | Weijand | 607/21 |
| 5,493,100 | 2/1996 | Renger | 219/497 |
| 5,509,424 | 4/1996 | Al-Ali | 600/505 |
| 5,692,514 | 12/1997 | Bowman | 600/526 |

FOREIGN PATENT DOCUMENTS 9117703  11/1991  WIPO ..................................... 600/526

*Primary Examiner*—Robert L. Nasser
*Attorney, Agent, or Firm*—Michael J. Jaro; Harold Patton

[57] ABSTRACT

Apparatus and method are provided for obtaining a measure of blood flow, and more specifically cardiac output, by analyzing blood temperature variations in the arterial tract. In a first embodiment, a lead carrying two closely spaced temperature sensors is positioned so that the sensors are in the atrial tract and produce temperature signals representative of small cyclical temperature variations of the blood outputted from the heart. The two signals have substantially similar patterns for each cardiac cycle, but the signals are separated by a short time ($\Delta T$) representative of the distance between the two sensors. The patterns are correlated to find $\Delta T$, from which cardiac output is calculated. In an alternate embodiment, a single blood temperature sensor is employed along with a sensor for determining cardiac contractions, and a measure of cardiac output is obtained by comparing the time difference between a feature of the blood temperature signal with the time of cardiac contraction.

15 Claims, 3 Drawing Sheets

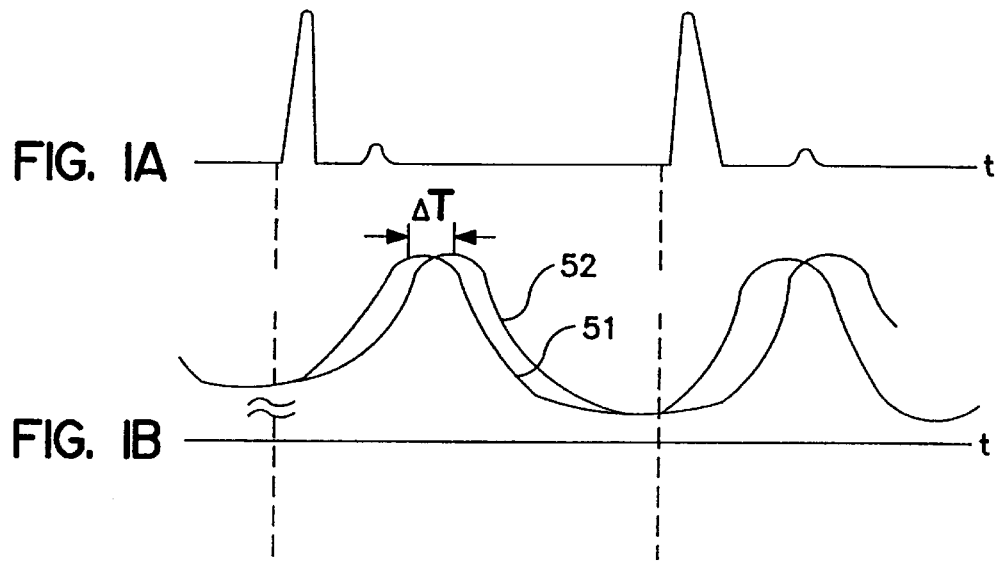
FIG. 1A
FIG. 1B
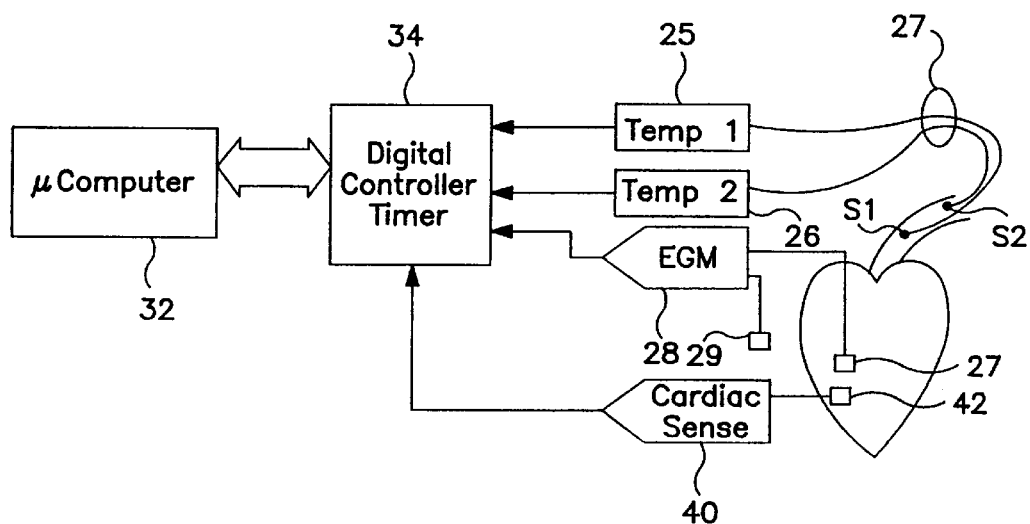
FIG. 2

FIG. 4A Cardiac event

FIG. 4B Blood sensor signal

CARDIAC FLOW SENSOR

FIELD OF THE INVENTION

This invention relates to cardiac flow sensors and, in particular, cardiac flow sensor apparatus based upon naturally occurring temperature variations in blood flow.

BACKGROUND OF THE INVENTION

The ability to measure cardiac output, or blood flow, has long been recognized as being of substantial use. Blood flow is defined as the volume of blood flow over a unit of time, and if measured at the output of the heart, is a measure of cardiac output. Measurement of blood flow is useful in conjunction with cardiac pacemakers, as well as cardiac defibrillators and other cardioverters, and cardiac diagnostic instruments.

A primary prior art method of determining blood flow is that of thermodilution, where a bolus of blood at an elevated temperature is generated, such as by heating the blood with an electrical current between a pair of electrodes. A temperature sensor located in the blood stream downstream from electrodes produces an output in accordance with a known thermodilution curve, providing means for measuring the rate of blood flow between the heating the blood and the measurement point. From this, flow, or cardiac output, can be determined.

More recently, other techniques for determining blood flow by thermal sensing have been disclosed. For example, in U.S. Pat. No. 5,174,299, the disclosed technique is that of heating the flowing blood, and measuring the temperature of the blood at two points. Assuming that the flow is inversely proportional to the temperature difference between the two points, the temperature difference can be correlated into blood flow. See also, for example, U.S. Pat. No. 5,493,100, representative of heating blood by coupling a drive signal to a thermistor placed in the blood stream, and then sensing subsequent time variations. However, these techniques require the complexity of generating heat within the blood stream in order to establish the measurement conditions.

It is known that the temperature of the blood in the heart varies cyclically, i.e., with systole and diastole. Blood that has passed through the lungs is relatively cooled due to exchange with the air, and then when it comes back into the heart it is heated by the cardiac muscle. After ejection of the blood, the heart is again filled with relatively new cool blood, which then warms until the next heart contraction, producing cyclical variations. Such temperature variations are rather small, in the order of less than 1° C., but can be detected by a fast time response sensor. These observations are the basis of U.S. Pat. No. 5,336,244, which discloses a pacemaker system having a fast response temperature sensor located in the heart for generating cycle-by-cycle variation of temperature indicative of heart contractions, enabling capture detection.

SUMMARY OF THE INVENTION

It is an object of this invention to utilize the small naturally occurring temperature variations in the bloodstream, and in particular the arterial blood stream, in order to provide a measure of blood flow and, in particular, cardiac output. By accurately measuring blood temperature variations at two closely spaced positions within an arterial vessel of substantially uniform cross-section, a cyclical measurement of blood velocity is obtained, which can be translated into a measurement of blood flow, and thus cardiac output. Alternately, temperature transients can be measured at a single arterial location, and the delay with respect to cardiac contraction can be determined for calculation of cardiac output.

In accordance with the above object, there is provided a system and method utilizing one or two fast response temperature sensors positioned in the aorta or elsewhere in a tract of the arterial circulation system just downstream from the left ventricle, for sensing on a cardiac cyclical basis naturally occurring temperature variations. The temperature variations are, as a first order approximation, sinusoidal and synchronized with the patient's heartbeats. For a two sensor embodiment, the sensors are spaced a short distance apart, e.g., several mm or about 1 cm, such that there is a small time delay, or phase delay between the variations of the two sensor signals. These two signals are processed by correlating them so as to compare the temperature signal patterns, and to thereby determine the time delay which is representative of blood flow. Using digital correlation techniques, the correlation of the signal patterns is accomplished with high accuracy. Note that it is not necessary for the sensors to be accurately calibrated, as only the small differences, or temperature variations are important.

In a preferred embodiment, a correlation in accordance with this invention is carried out by digital sampling of the respective temperature signals, the sampling being initiated by sensing a cyclical cardiac event such as the QRS. The sampling provides two temperature signals referenced in time, for each cardiac cycle, which are then correlated by any standard computational technique. In one embodiment, a Fast Fourier Transform (FFT) is carried out on each signal, and the time delay between the two signals which produces an optimum correlation is determined. The measured time delay, or delta time, is calculated cyclically or an average delta time is calculated over a predetermined number of cardiac cycles.

In another embodiment, a single temperature sensor is used to obtain a signal representative of the variations in blood temperature. A second sensor (pressure or EKG) is used to detect cardiac contractions. The time delay between cardiac contraction and a characteristic point of the temperature variation provides an indication of cardiac output.

BRIEF DESCRIPTION OF THE DRAWINGS

FIG. 1A is a timing diagram illustrating cardiac electrical signals; FIG. 1B is a timing diagram illustrating curves S1 and S2, representative of respective temperature variations detected by a pair of sensors spaced within the patient arterial tract, illustrating how the signals can be correlated to determine the time delay ($\Delta T$) which is representative of flow rate through the artery, and thus of cardiac output.

FIG. 2 is a schematic diagram showing the primary components of the invention in relation to the patient's heart and arterial tract.

FIG. 4A is a timing diagram illustrating sensed signals representative of heart contractions; FIG. 4B is a timing diagram illustrating blood flow temperature sensed in the arterial tract.

DETAILED DESCRIPTION OF THE PREFERRED EMBODIMENTS

Figure 3:
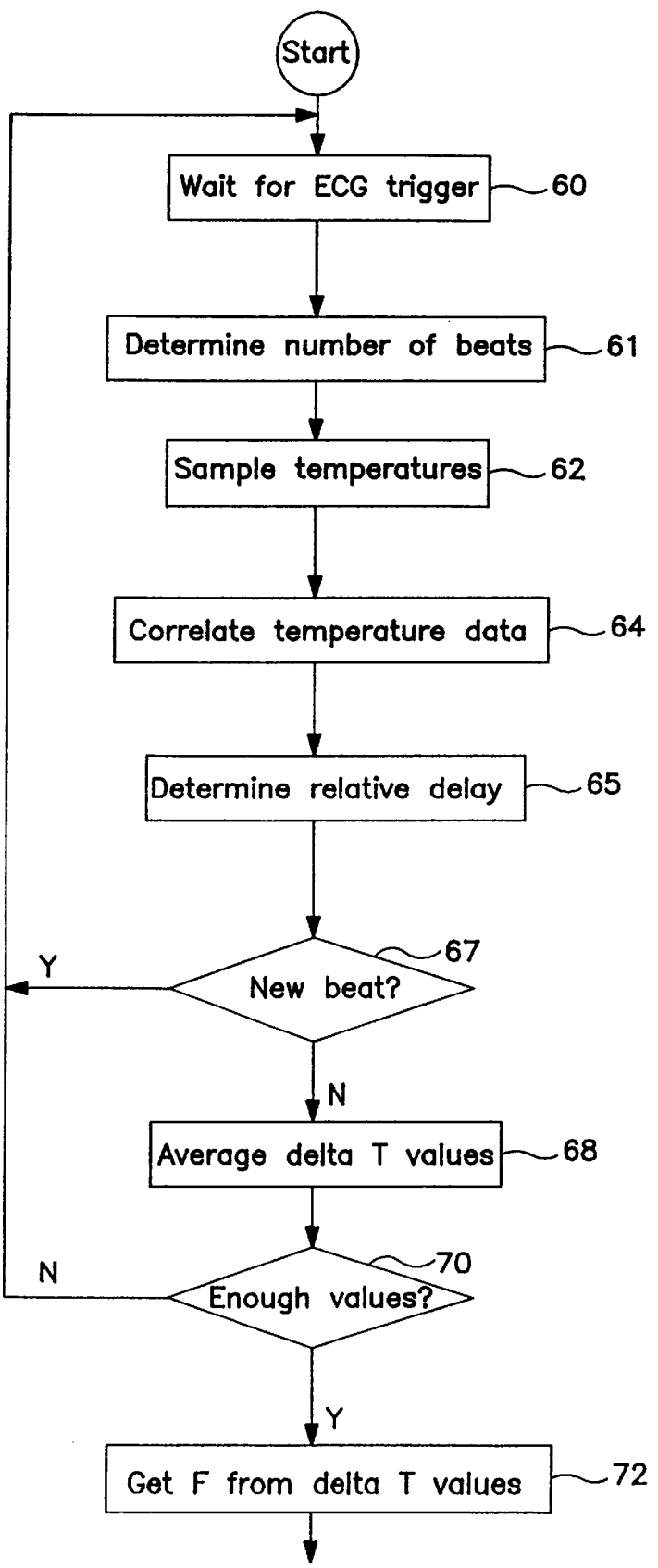
FIG. 3 is a flow diagram illustrating the primary steps carried out by the system of this invention in obtaining and correlating temperature data from two closely spaced sensors, and deriving a measure of cardiac flow from computed average delta time between the two temperature signals.

Referring now to FIG. 1A, there is shown a timing diagram of a typical ECG, showing cardiac heartbeats. Heartbeats may be naturally occurring, or they my be evoked by delivered pacemaker pulses. FIG. 1B shows representations of two sensor signals, illustrated as S1 and S2, in timed relation to the heartbeats of FIG. 1A. S1 represents a first sensor positioned closest to the patient's ventricular output, while S2 represents a second sensor output, where the second sensor is positioned a short distance downstream from the first sensor, as is illustrated in FIG. 2. It is to be understood that FIG. 1B shows in expanded form the small, natural time variation of blood temperature at the two locations, and does not depict base blood temperature. Operating with the premise that the arterial cross-section between the two sensors is substantially constant, the signal patterns of S1 and S2 are substantially the same. However, the signal S2 is delayed in time by an amount delta T, due to the fact that it is positioned at bit further downstream from the sensor that produces signal S1. It can be seen that the signal patterns of the curves S1 and S2 are substantially the same, the distance between the sensors being small enough that there is no significant difference in the variations of the signals. Based on this observation, the technique of this invention is to determine the time difference, $\Delta T$, by which either signal need be shifted with respect to the other to provide an optimum correlation; this is done by finding the $\Delta T$ corresponding to peak correlator output. This time difference is used to calculate flow (F), as discussed further below.

Referring now to FIG. 2, there is shown a block diagram illustrating the primary apparatus components of the blood flow measurement system of this invention. It is to be understood that the system may be usefully part of a cardiac pacemaker or other cardiac-related implanted devices, or it may be a stand-alone unit. Likewise, this system may be entirely implantable, or the electronics portion may be external. As illustrated, two temperature sensor circuits 25 and 26 receive temperature signals from sensors S1 and S2 which are carried on a lead illustrated at 27. Lead 27 has a pair of conductors, each of which carries a temperature signal produced by one of the sensors S1, S2 to a proximal output terminal. The temperature sensors are fast operating, with time constants substantially less than 100 ms, and preferably less than 50 ms. The sensors are suitably coated, e.g., with a collagen, to minimize growth of tissue on the sensor surface, so as to optimize time response. The sensors are preferably positioned only several mm, or up to 1 or 2 cm apart, on lead 27. Lead 27 is positioned such that the sensors S1 and S2 are placed within the aorta, or in the arterial tract. As used herein, arterial tract refers to an arterial location sufficiently close to the heart output that the naturally occurring blood temperature variations in the heart are substantially undissipated. Each temperature sensing circuit 25, 26 is connected to one of the lead output terminals, and has conventional circuitry for providing an amplified, filtered analog temperature signal, which in turn is outputted to digital controller timer circuit 34. The design of the temperature sensing circuitry is not critical to the invention, and very suitable designs are known to those skilled in the art. Also shown is a sensor 42 positioned in the heart, and cardiac sense circuitry 42 which processes the heart sensor signal and connects it to circuit 34, as discussed below in connection with the embodiment of FIGS. 4A–4C. Digital controller/timer circuit 34 is a conventional circuit such as utilized in implantable cardiac pacemakers. It digitizes the temperature signals from the respective temperature circuits to obtain from each signal a digital representation of the variation of blood temperature during each cardiac cycle. These digital signals are coupled to microprocessor 32, which accumulates digital data corresponding to each cardiac cycle, and then processes it as discussed in further detail in connection with FIG. 3. Digital controller timer 34 also receives a signal from EGM signal circuit 28, which receives an EGM input from either one or a pair of electrodes illustrated in the patient's heart at 27, or a pair of EKG electrodes as illustrated at 29. The criteria for the electrodes is simply that they make available a signal of cardiac events corresponding to the timing signal of FIG. 1A, which is then processed in conventional circuit 28 and coupled to the circuit 34. The cardiac signal information is likewise passed through to microprocessor or microcomputer circuit 32. Circuit 32 may be a conventional microprocessor with a system clock and RAM and ROM storage, and may include any additional amount of memory required to carry out the process of the invention, and use the determined flow data in programmed applications.

Referring now to FIG. 3 there is shown a flow diagram of the primary steps carried out by the system of this invention, preferably by a microprocessor as illustrated in FIG. 2. At the start of the flow measurement, the routine waits for an ECG trigger, as illustrated at 60. When this arrives, through circuit 34 from EGM circuit 28, the routine goes to 61 and determines the number of beats. This number is initialized to 0 at the start, and is incremented each cycle until reset. After this, at block 62, the routine obtains the digital data representative of the sampled temperature signals from the two sensors, for the cycle being examined. At 64, the microprocessor routine correlates the temperature data from the two different sensors. Only related events that occur in both sensors result in an output from the correlator. Note that it is known that each sensor signal has only one peak and one trough per cycle, due to the principle of cyclical heating and cooling as discussed above. However, because of the small temperature differentials involved, and the potential that the signal can be very noisy, it would be extremely difficult to determine the peak and the trough of either sensor signal. Thus, the step of correlation is an important one for carrying out the subject invention. Only related events that occur in both sensors result in an output from the correlator. Note that the absolute temperature, or total amplitude of either sensor signal is not important, as it is only cyclical variations that are being measured. Consequently, patient temperature variations, as with a fever, are not a problem.

The correlation function can be done by any suitable correlation computation. Correlation is a form of convolution, and can involve significant time consuming calculations. Since these calculations are energy consuming, any implementation which reduces these calculations is useful, particularly for an implantable device. In this invention, instead of convolving the two time signals, convolution in the time domain can replaced by multiplication in the frequency domain of the frequency representations of the two signals. Then, an inverse FFT is applied to the result of the multiplication, to obtain a time domain representation of the convolution of the original two signals. Due to the relatively simple nature of the variation of each signal, it is known that the result contains only three significant frequency components. This means that the inverse FFT step need be performed only on three frequency components, such that the frequency domain conversion of the two Fourier Transforms, can be reduced to a discrete frequency transform. At 65, the relative delay, or $\Delta T$ value for the optimal correlation is determined, i.e., where the peak in the correlation function is determined. At 67, a decision is made as to whether the correlation should be made corresponding to a next beat. If yes, the routine loops back to 60 and repeats the loop. If no, the routine goes to 68 and computes an average of the ΔT values for the number of beats that had been accumulated at block 61. Next, at block 70, a determination is made as to whether enough values were obtained to get an acceptable average ΔT. Thus, if the average value obtained at step 68 is determined to be out of limits and thus unreliable, the routine loops back to 60 and starts over again. However, if it is reliable, the routine proceeds to block 72 and makes a calculation of flow (F) from the average ΔT value. This calculation is straightforward, and includes an appropriate coefficient, or factor, which is stored in memory. Note the ΔT represents average flow over the cardiac cycle; since the cross-section of the artery is presumed to be the same as the two sensor locations, flow is proportional to the average ΔT value.

Figure 4C:
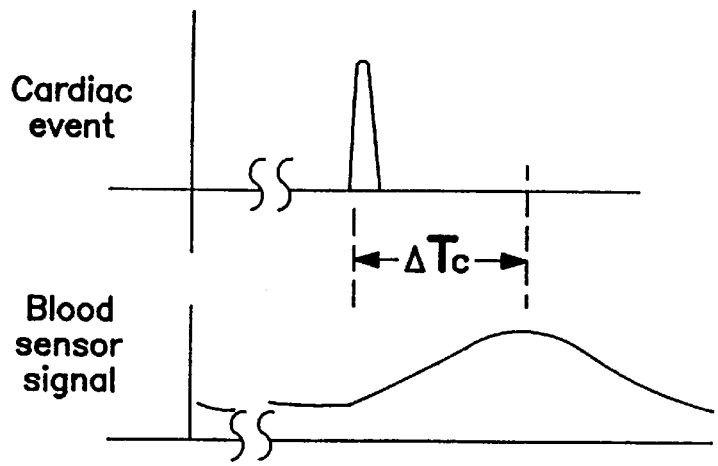
FIG. 4C is a simplified flow diagram of the process of determining cardiac output by comparing the sensed blood temperatures variations with the timing of cardiac contractions.
Figure 4C:
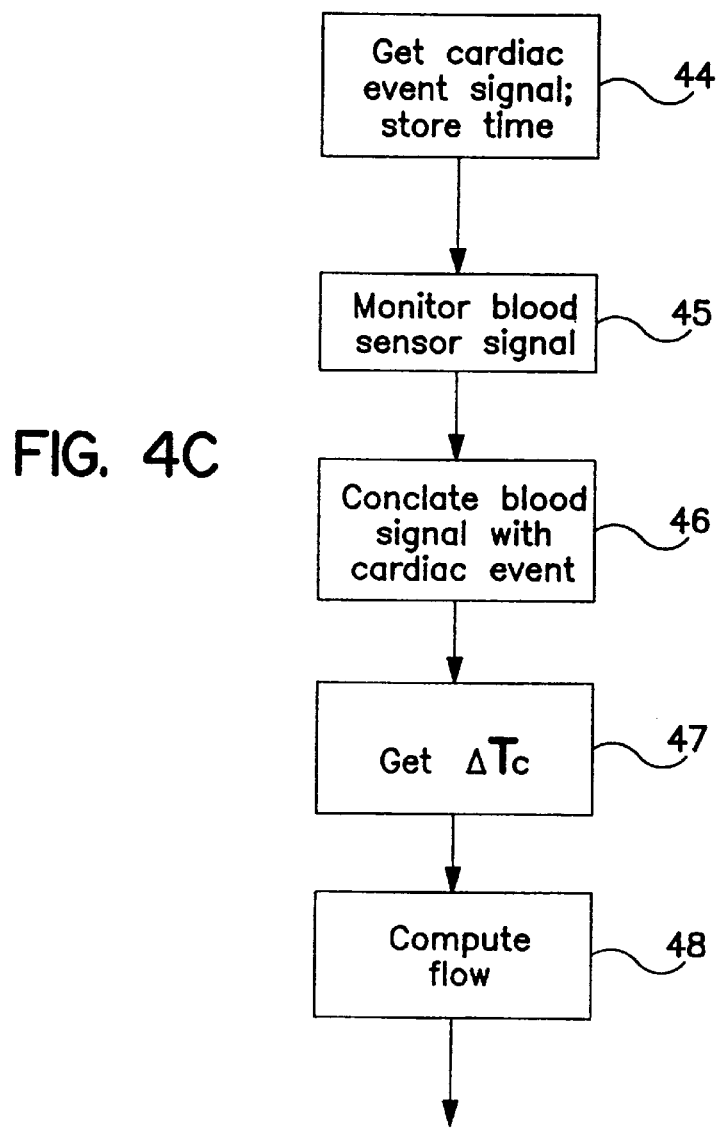

Referring now to FIGS. 4A, 4B and 4C, there is illustrated another embodiment of the invention, based on the principle that blood flow can be determined from the time delay between arterial temperature transients and the cardiac contraction. For example, the blood temperature variation at a single sensor location in the arterial tract can be correlated with a sensed QRS, to determine a measure of blood flow. As seen in FIG. 4A, there is illustrated a cardiac event, such as a QRS. Cardiac events could also be sensed by measuring another variable, such as ventricular pressure, myocardial contractility, or even peak blood temperature sensed in the ventricle. Thus, sensor 42, as illustrated in FIG. 1, may be any suitable sensor for sensing a heartbeat. Similarly, a delivered cardiac pace pulse can be used as indicative of the cardiac contraction. The timing diagram of FIG. 4B illustrates variations in sensed blood temperature at a point just downstream from the cardiac output. This may be provided by a single temperature sensor, such as S1 or S2 illustrated in FIG. 1. This embodiment involves measuring the time between the cardiac event, as illustrated in FIG. 4A, and the resulting change measured by the single sensor in the outflow tract. Thus, in a most simple form, this embodiment would constitute measuring the peak of the blood temperature signal illustrated in FIG. 4, and determining therefrom the time delay $\Delta T_C$ between the cardiac contraction and the signal peak. In a more complex embodiment, the time differential is measured by correlating the temperature signal with the heart contraction, using stored correlation data.

Referring to FIG. 4C, there is shown a simplified flow diagram of a method of obtaining a measure of blood flow, by comparing a single blood temperature signal with the just prior cardiac contraction. As illustrated at step 44, in this routine the cardiac event signal is obtained and the time of the cardiac event is stored. Thus, the ECG can be monitored to obtain the time of the QRS, or another cardiac parameter can be sensed and analyzed to obtain an indication of cardiac contraction. Next, as indicated at step 45, the blood temperature signal is monitored, e.g., a temperature signal is obtained at one arterial sensor. At 46, the timing of the cyclical blood temperature signal is compared with the timing of the cardiac event. Thus, for example, the optimum correlation of the signal peak value with a sensed QRS can be obtained. At 47, the time differential $\Delta T_C$, corresponding to the optimum correlation, is obtained, and at 48 a measure of flow, or cardiac output is obtained as a function of $\Delta T_C$.

While the preferred embodiments have been disclosed, it is to be understood that other variations of the invention can be designed, within the scope of the invention as described.

Thus, while correlation of the signals is preferred, other computational techniques can also be used. Further, more than two sensors can be used, along with a more sophisticated algorithm for computing flow.

We claim:

1. A system for determining a measure of arterial blood flow from the heart, comprising:

a sensor lead having thereon a pair of fast time response temperature sensors positioned a short distance apart on said lead, said lead having output terminals and conducting means for conducting said temperature signals from each of said sensors to respective ones of said output terminals;

processing means for receiving said signals from said output terminals and for processing same to derive sets of digital representations of each of said temperature signals;

correlation means for finding the time delay between said two temperature signals at which said signals optimally correlate; and computational means for computing from said time delay a measure of blood flow.

2. The system as described in claim 1, comprising output means for determining a measure of cardiac output from said blood flow measure.

3. The system as described in claim 1, comprising EKG means for obtaining cardiac signals representative of cardiac electrical activity, and wherein said processing means comprises cyclical means triggered by said cardiac signals for deriving said digital representations corresponding to respective cardiac cycles.

4. The system as described in claim 3, wherein said correlation means comprises means for performing a correlation in the frequency domain on each set of digital representations for each cardiac cycle.

5. The system as described in claim 1, wherein said sensors are positioned apart by a distance no greater than 2 cm.

6. The system as described in claim 1, where each of said sensors has a time response of less than 100 ms.

7. A method of determining cardiac output of a patient, comprising:

positioning first and second fast response sensors in the patient's arterial tract, said sensors being positioned a short distance from each other along the axis of the atrial tract;

obtaining naturally occurring cyclical temperature signals from each of said sensors corresponding to respective cardiac cycles;

processing said cyclical signals to obtain therefrom a measure of flow rate; and determining cardiac output from said flow rate measure.

8. The method as described in claim 7, comprising performing correlation operations on pairs of said cyclical temperature signals.

9. The method as described in claim 7, comprising fixing said short distance in a range of about 1 mm to no more than 2 cm.

10. The method as described in claim 7, comprising obtaining cardiac electrical signals, and using said cardiac electrical signals to initiate said cyclical temperature signals.

11. A cardiac flow measurement system, comprising:

sensor means for providing cyclical signals representative of naturally occurring blood temperature variations of blood in the patient's arterial tract; and processing means for processing said signals to obtain a measure of blood flow from the patient's heart.

12. The system as described in claim 11, wherein said sensor means comprises at least two fast time response sensors.

13. The system as described in claim 12, wherein said sensor means comprises lead means for carrying said two sensors at a fixed distance from each other no greater than about 2 cm.

14. The system as described in claim 13, wherein said processing means comprises correlation means for providing an indication of the time differential between the two signals from said two sensors.

15. The system as described in claim 14, wherein said sensors have time responses of less than 100 ms.

* * * * *